(12) United States Patent
Krattiger et al.

(10) Patent No.: US 6,500,115 B2
(45) Date of Patent: Dec. 31, 2002

(54) ENDOSCOPE

(75) Inventors: Beat Krattiger, Beringen (CH); Harald Haan, Schaffhausen (CH); Manfred Kuster, Schaffhausen (CH); Pavel Novak, Schaffhausen (CH); Jörg Reling, Weilheim (DE)

(73) Assignee: Storz Endoskop GmbH (CH)

( * ) Notice: Subject to any disclaimer, the term of this patent is extended or adjusted under 35 U.S.C. 154(b) by 134 days.

(21) Appl. No.: 09/795,816

(22) Filed: Feb. 28, 2001

(65) Prior Publication Data

US 2001/0018553 A1 Aug. 30, 2001

Related U.S. Application Data

(63) Continuation of application No. PCT/EP99/06142, filed on Aug. 20, 1999.

(30) Foreign Application Priority Data

Aug. 28, 1998 (DE) .......................................... 198 39 188

(51) Int. Cl.[7] .............................................. A61B 1/005
(52) U.S. Cl. ...................... 600/173; 600/131; 600/137; 600/138; 600/171
(58) Field of Search .............................. 600/131, 137, 600/138, 171, 173

(56) References Cited

U.S. PATENT DOCUMENTS

| | | | |
|---|---|---|---|
| 4,874,371 A | 10/1989 | Comben et al. | 604/95 |
| 4,902,129 A * | 2/1990 | Siegmund et al. | 33/377 |
| 5,156,142 A | 10/1992 | Anapliotis et al. | 128/6 |
| 5,184,602 A | 2/1993 | Anapliotis et al. | 128/6 |
| 5,254,117 A * | 10/1993 | Rigby et al. | 606/42 |
| 5,702,349 A | 12/1997 | Morizumi | 600/131 |
| 5,762,603 A | 6/1998 | Thompson | 600/112 |
| 5,868,785 A * | 2/1999 | Tal et al. | 600/564 |

FOREIGN PATENT DOCUMENTS

| | | |
|---|---|---|
| DE | 190703 | 11/1907 |
| DE | 2625699 | 12/1977 |
| DE | 3943403 | 7/1991 |
| DE | 19839188 | 3/2000 |
| EP | 0117894 | 9/1984 |
| EP | 0369937 | 5/1990 |
| EP | 0682901 | 11/1995 |
| GB | 2138687 | 10/1984 |

* cited by examiner

*Primary Examiner*—John Mulcahy
(74) *Attorney, Agent, or Firm*—St. Onge Steward Johnston & Reens LLC

(57) ABSTRACT

An endoscope is provided having a shaft and a handle extending to the side of the shaft at the proximal end. A mechanism is provided for pivoting the view direction in an observation area and has at least one operating element being engaged with the mechanism for actuating the mechanism. The at least one operating element is positioned on the handle, such that the mechanism is actuatable with at least one finger or thumb of the same hand holding the handle.

22 Claims, 6 Drawing Sheets

ENDOSCOPE

CROSS REFERENCE TO PENDING APPLICATION

This application is a continuation of pending International application PCT/EP99/06142 filed on Aug. 20, 1999, which designates the United States.

BACKGROUND OF THE INVENTION

The invention relates to an endoscope having a shaft and a handle extending sideward from the shaft and arranged at a proximal end. A mechanism is provided for pivoting the direction of view in an observation area and at least one operating element is engaged with the mechanism for actuating the same.

An endoscope of this type is disclosed in the German brochure of Olympus Optical Co. (Europa) GmbH, Hamburg, "OLYMPUS—THE VISIBLE DIFFERENCE" with the designation "Schwenkprisma-Boreskop" (["Borescope with pivotable prism"]).

Endoscopes are becoming more important both in technical as well as medical applications. In technical fields, such endoscopes allow an inexpensive, non-destructive, visual control of material quality. Difficultly accessible cavities and hidden components can be visually inspected with an endoscope without time-consuming disassembly. A further application of technical endoscopes is in the study of combustion processes in internal combustion engines, turbines or reactors, only to name a few.

In the medical field, endoscopes are employed in minimally invasive surgery. Operations without larger incisions can be carried out under visual control with the endoscope, where the patient is only slightly affected.

It will be understood that the viewing direction is the direction of the symmetry axis of the light cone, limited by the image angle, of the observation light entering the distal end of the shaft. In a simple type of the known endoscopes, the view direction is fixed and can only be altered by changing the position of the endoscope, which however is only possible to a limited extent. Thus to observe an object from different perspectives or to enlarge the viewing area, i.e. the view field, separate endoscopes having different optics have been provided. These include for example optics for a forward view, a view slightly displaced from forward, side view and rear view. These types of endoscopes must be exchanged with one another during an operation to alter the view direction, which however is inconvenient. For each exchange, the one endoscope must be withdrawn from its entry opening into the observation area and the next endoscope must then be inserted.

Endoscopes of the type mentioned at the outset have been developed with a mechanism for pivoting the view direction at least in the circumferential direction of the shaft. With one single endoscope, an object can be inspected from different perspectives or a larger region can be seen in the observation area. Thus the view direction can be altered without changing the position of the endoscope.

The endoscope known from the above company brochure comprises a handle projecting from a side of the shaft at its proximal end. The handle can be comfortably held in the hand, since it can be readily gripped by the fingers and the thumb when placed in the hand. An operating element is provided which operatively engages with the mechanism for pivoting the view direction, so that the desired direction can be adjusted by actuating the operating element.

The operating element in the known endoscope is provided as an adjustment ring, which is arranged concentrically with the axis of the shaft near the ocular. This configuration of the endoscope has drawbacks with respect to its operational capabilities. When the endoscope is held in the one hand, the other hand must be used to actuate the operating element to pivot the view direction. It is not possible or it is very difficult to operate the ring with the same hand holding the handle, because the ring is positioned above and behind the hand handle. In addition, actuating such an adjustment ring normally requires the use of the thumb and the index finger. The view direction and the image focus cannot be adjusted simultaneously, because no hand is free for actuating the focusing ring at the time the operating element is being used to pivot the view direction.

Since the ring is not ergonomically positioned on the handle and the ring is formed to be concentric with the shaft, the endoscope cannot be held in one hand and simultaneously the ring actuated with the same hand. Thus it is not suited for one-hand operation.

An object of the present invention, therefore, is to provide an endoscope of the above-mentioned type, in which the operational capabilities of the endoscope are improved.

SUMMARY OF THE INVENTION

According to the present invention, an endoscope is provided, comprising:

- a shaft having a longitudinal axis, a distal end and a proximal end;
- a handle disposed at said proximal end of said shaft and extending sidewards of said shaft, said handle being configured in pistol-like fashion;
- a mechanism for pivoting a view direction of said endoscope within an observation area; and
- at least two operating elements which are operatively engaged with said mechanism for actuating said mechanism, a first one of said at least two operating elements being for pivoting said view direction with respect to said longitudinal axis of said shaft and the second one of said at least two operating elements being for pivoting said view direction in circumferential direction, said first operating element being disposed on a front side of said handle such that it is operable with at least one finger of the hand holding said handle, wherein said second operating element is disposed on a side face of said handle such that it is operable with the thumb of said same hand holding said handle.

The endoscope of the present invention allows a one-hand operation, not possible in the known endoscope, through the configuration with at least two operating elements positioned on the handle itself, one on the front side and one of the side face of the handle, so that the one can be actuated with at least one finger and the other with the thumb of the same hand holding the handle. The positioning of the operating elements on the handle allows the handle to be held firmly in the hand while actuating the operating elements and the operating elements to be actuated without substantial change in the position of the hand or in the manner of gripping. The sidewardly extending handle thus remains comfortably held in the hand also when actuating the at least one operating element. The invention is therefore to position at least two operating elements on the handle at a location where the thumb and at least one finger lies when normally gripping the handle in relaxed manner. An advantage is that the operating elements can be actuated with only slight movement of a finger and thumb. The endoscope of the present invention is considerably improved in handling due to the one-hand operability.

Positioning one of the elements at the front side has the advantage that the operating element can be actuated with the fingertips or the forward finger joints of one or more fingers of the same hand holding the handle. A further advantage is that the endoscope can be operated by left as well as right-handed persons, because the operating element can be provided at a central position on the distal side of the handle.

At least two operating elements are provided, where the at least one operating element for pivoting the view direction with respect to the longitudinal direction and the at least one further operating element for rotating the view in circumferential direction are positioned with respect to one another such that one the operating elements is actuated with the thumb and the other with at least one finger of the same hand which holds the handle.

With this configuration, the view direction with respect to the longitudinal axis of the shaft is pivoted by adjusting the disposition of the optical element, i.e. the view direction relative to the longitudinal axis is adjusted by adjusting the disposition of the optical element in an angular range between for example a forward view and a rear view. On the other hand, by rotating the shaft the view direction is altered in circumferential direction of the shaft. The known endoscope mentioned in the introduction comprises such a rotatable shaft and a pivotal prism. However, for rotating the shaft and for pivoting the prism, a ring is arranged concentrically about the shaft, which as already mentioned cannot be operated by the same hand holding the handle.

In contrast, a one-hand operation of two operating elements is achieved in the present invention, because these operating elements are ergonomically positioned on the handle. A considerable advantage of the invention is that an arrangement is provided through the position of the operating element for rotating the shaft and the operating element for adjusting the optical element, which allows a simultaneous actuation of both operating elements. The one operating element can be actuated for example with the index finger and the further operating element with the thumb, such that the desired view direction can be adjusted more easily and much faster, which is not possible with the known endoscope.

The object underlying the present invention is thus completely achieved.

In a particularly preferred embodiment, the first operating element is configured as a pistol-like trigger.

In combination with the positioning of the first element on the front side of the handle, this has the advantage that the trigger can be operated over a small distance and therefore operated with slight finger movement by bending the finger. The trigger, which can be formed as a pivot lever, can preferably be actuated with the index finger, while the remaining three fingers and the thumb comfortably hold the handle. This configuration of the operating element is therefore particularly ergonomic.

In a further preferred embodiment, the first operating element is formed as a button.

A one-hand operation is also advantageously achieved with this configuration. The button can be positioned on a side face of the handle to be operated with the thumb or as mentioned above, positioned on the front side of the handle to be operated with one finger of the hand grasping the handle. In a configuration with a pair of buttons, one button is preferably configured to pivot the view in one direction and the neighboring button to pivot in the opposite direction. In a configuration as a toggle button, one side of the button is preferably for pivoting the view in one direction and the other side for pivoting in the opposite direction.

In a further preferred embodiment, the first operating element comprises a circumferentially closed or partially open ring for actuation with one or more fingers.

The feature has the advantage if the operating element is not moved against a return force, so that the element can be moved back and forth with the same finger or fingers or with the thumb without having to reposition the finger or fingers.

In a further preferred embodiment, the second operating element is formed as a slide member and is arranged on the at least one side face of the handle.

The feature represents a further advantageous possibility of positioning and configuring the operating element, which enables actuation with the thumb alone. If such a slide member is provided on both side faces of the handle, the present endoscope can then advantageously be operated with the left or right hand.

In a further preferred embodiment, the second operating element is configured as an adjustment wheel, which is rotatably mounted in the handle, where the handle includes at least one window on at least one of its side faces in which a portion of the circumference of the adjustment wheel is exposed.

An advantage is that the adjustment wheel, of which only an operable portion protrudes from the handle, can be rotated with the thumb with only slight thumb movement. Preferably, an actuatable portion of the adjustment wheel is exposed on both sides of the handle, so that the endoscope can be operated with the left or the right hand in the same manner.

In a further preferred embodiment, the adjustment wheel is arranged in the handle with its pivot axis not being parallel to the longitudinal axis of the shaft.

An advantage is that the direction of operation of the adjustment wheel runs approximately in the direction of the shaft axis. This operation direction is advantageously adapted to the freedom of movement of the thumb when the handle is grasped by the hand of the user.

In a further preferred embodiment, the mechanism for pivoting the view direction comprises at least one optical element arranged to be adjustable in position at the distal end of the shaft, where the position adjustment provides pivoting of the view direction substantially with respect to the longitudinal direction of the shaft and the first operating element is operatively engaged with the optical element.

In combination with the positioning of the at least two operating elements on the handle, an advantageous one-hand operation of the pivoting of the view direction is achieved with respect to the longitudinal direction, for example between a forward and rearward view direction.

In a further preferred embodiment, the mechanism provides rotatability of the shaft, where the shaft is rotatable about its longitudinal axis to pivot the view direction in circumferential direction and wherein the second operating element is operatively engaged with the shaft for rotating the shaft.

In combination with the position of the at least one operating element on the hand handle, an advantageous one-hand operation for rotating the view direction is achieved also in the circumferential direction.

In a further preferred embodiment, at least one of the first and second operating elements is configured to be self-retarded.

An advantage of this feature that an adjusted view direction is maintained without the one and/or the other operating element needing to be held fixed. An additional advantage is that an undesired displacement of the view direction is avoided.

In a further preferred embodiment, at least one of the first and second operating elements can be locked in at least one operating position.

An advantage is that at least one view direction, preferably however any view direction, adjusted with the operating elements, can be locked in place, so that when interrupting an inspection, the inspection can be started again with an unaltered view direction and a desired location being observed can be immediately found again. The locking of the operating element for rotating the shaft is preferably achieved by a catch of the operating element which can be engaged and disengaged.

In a further preferred embodiment, at least one display means is provided for displaying the respectively adjusted view direction.

An advantage is that the user of the endoscope can determine and document the position of an object with respect to other observed objects or with respect to points in the observation space in the manner of a bearing. This is possible based on the adjusted view direction being displayed as an angle with respect to a fixed direction, for example an axis of the endoscope.

In a further preferred embodiment, the display means is arranged in the image transmission path of the endoscope, so that the adjusted view direction is displayed in a viewfinder image in the optics of the endoscope.

An advantage is that the adjusted view direction can be particularly conveniently determined by simply looking through the endoscope.

Preferably, the display means comprise a disc-like element having reference markings distributed about its circumference and a pointer running about the longitudinal axis of the shaft relative to the markings.

This is an advantageous configuration of the display means for displaying a view direction in circumferential direction, by which the pointer moves about the shaft when it is rotated, while the disc-like element, for example in the form of a compass with reference markings, remains fixed when rotating the shaft. The element comprising the reference markings is preferably a shutter in the image transmission path of the endoscope. The reference markings can also be denoted with numbers in degrees, for example in steps of 30°. By simultaneously displaying the markings and the pointer, the angle between the handle and the circumferential view direction can at least be estimated and is also adjustable. For example, when holding the handle in vertical position, the vertical axis becomes the reference axis and the circumferential view direction is therefore defined. A location to be observed can be advantageously found again in this manner, or the observation direction, at least in circumference, can be estimated and documented.

In addition, the display means preferably comprises a bubble in a fluid for indicating the vertical direction.

This feature has the further advantage that the ground vertical direction is always defined by the bubble position, as in a level, during handling of the endoscope even when the handle is tilted slightly to the side. The bubble indicator can be provided in place of or in addition to the above-mentioned reference markings.

In a further preferred embodiment, the display means comprises a digital or analog display of the adjusted view direction.

An exact display of the respective view is advantageously made possible, namely a display can be provided for the view with respect to the longitudinal direction and/or the circumferential direction. The display can also be made visible in the image transmission path of the optics in the view field.

In a further preferred embodiment, the display means comprise one or more display windows arranged on the handle with digital or analog displays for the adjusted view direction.

This feature has the advantage that the adjusted view with respect to the longitudinal direction and/or in circumferential direction is shown on the handle itself, so that operational conditions of the endoscope with respect to the adjusted view direction can be recognized at any time.

In a further preferred embodiment, the handle projects from the shaft to be inclined with respect to the shaft toward the distal end.

With this configuration of the handle, an ideal ergonomic form is achieved, which is adapted for the purposes of manipulation of the endoscope. Namely, when using the endoscope, the ocular cup is drawn close to the eye of the user, so that the lower arm is closely adjacent to the upper arm. Due to the handle being inclined toward the distal end, the handle can be held in relaxed, tire-free manner with the wrist being angled slightly backwardly and upwardly.

In a further preferred embodiment, a connector for connecting an optical cable is arranged to be sunk in the handle, where the handle comprises an opening at least on one side at the position of the connector.

The connector being recessed or sunk in the handle has the advantage that the end of the cable, normally reinforced with a sleeve to protect against bending, is completely recessed into the handle, so that only the flexible portion of the optical cable extends from the handle. This has the advantage that the reinforced portion of the cable end does not hinder the use of the endoscope, whereby the utilization of the endoscope is further improved. The at least one opening provided on one side, preferably however two openings in the vicinity of the connector, allow easy handling for fixing and releasing the optical fiber connector.

In a further preferred embodiment, a TV camera is integrated at the proximal end of the endoscope.

The camera can be integrated at the proximal end of the handle in place of the normal ocular, so that the region to be observed can advantageously be made visable on a monitor.

The above advantages of the endoscope according to the present invention can be employed in technical endoscopy, but also in medical applications, particularly endoscopic surgery, in advantageous manner.

Further advantages will become apparent from the following description and the attached drawings. It will be understood that the above-mentioned features and those to be discussed below are applicable not only in the given combinations, but also in other combinations or taken alone without departing from the scope of the present invention.

Selected embodiments are shown in the drawings and will be discussed in more detail below with reference to the figures.

DETAILED DESCRIPTION OF PREFERRED EMBODIMENTS

Figure 1:
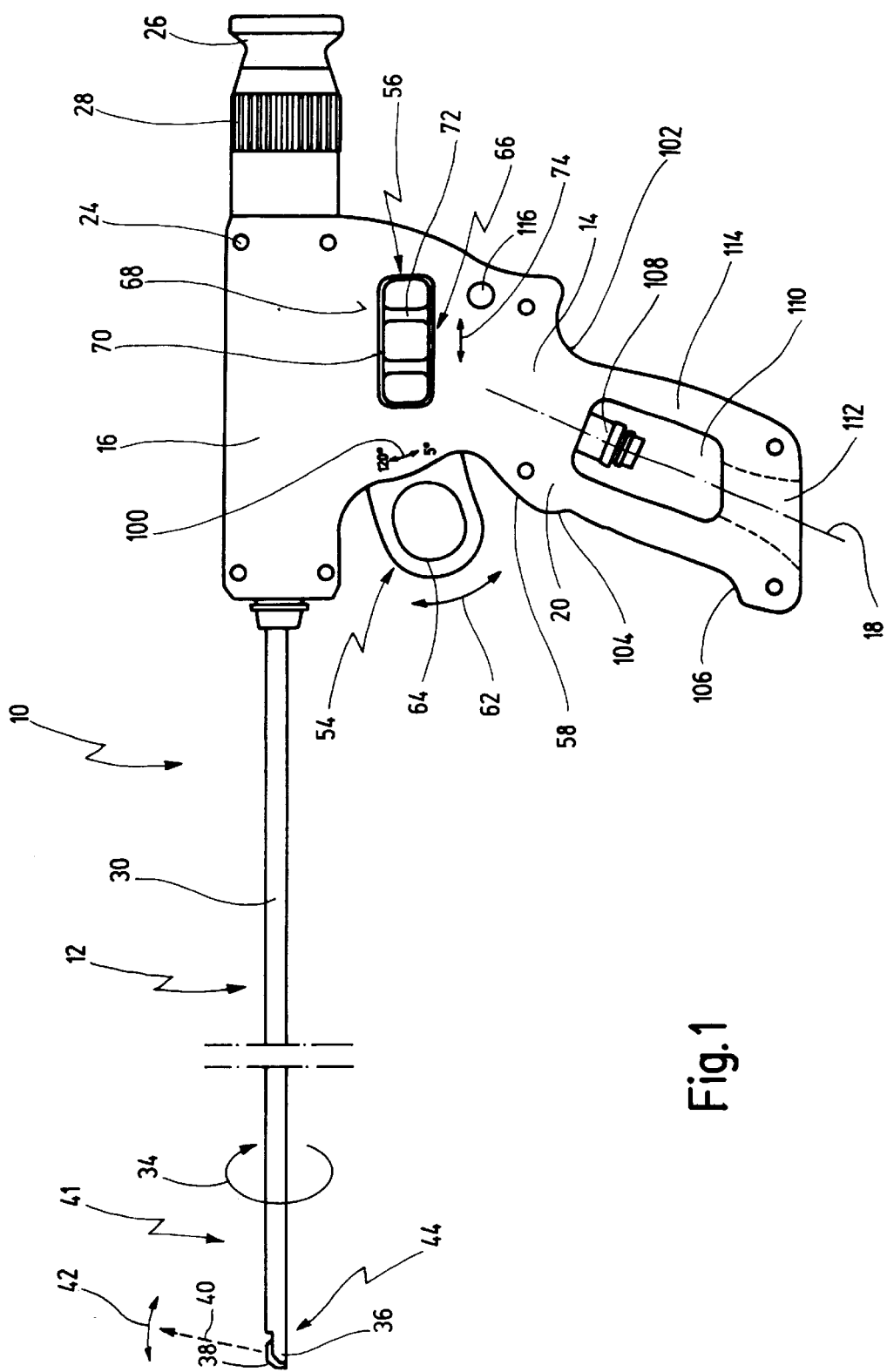
FIG. 1 shows a total representation in side view of an endoscope according to the present invention.

FIG. 1 shows an endoscope generally designated with the numeral 10. The endoscope 10 is used in technical endoscopy for inspection of cavities and objects contained therein, which are not or only difficultly accessible for observation with the naked eye. The endoscope 10 however can also be designed for medical applications in endoscopic surgery.

The endoscope 10 comprises a shaft 12 and a handle 14, which is secured to the shaft by a housing 16 integrally formed with the handle 14. The handle 14 extends to the side from the shaft 12, namely such that the handle 14 is inclined away from the shaft 12 and toward the distal end. The inclination of the handle 14 is indicated by a center axis 18 of the handle 14.

Figure 3:
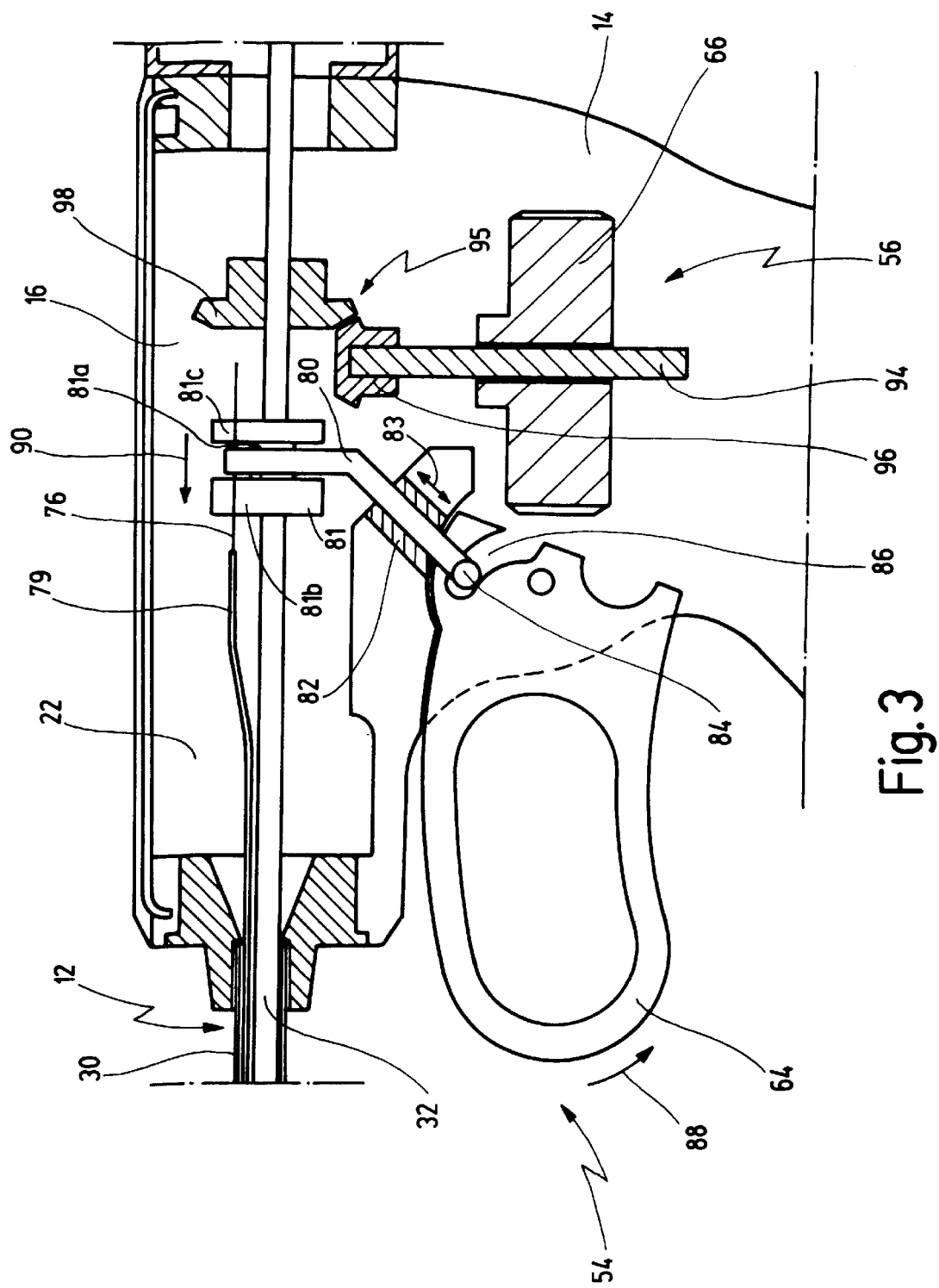
FIG. 3 shows a schematic representation to enlarged scale of the endoscope in FIG. 1 in the region of the handle, where the handle is opened.

The handle 14 and the housing 16 formed integrally therewith are formed of two half-shells 20, 22. The left half shell 20 is shown in FIG. 1 and the right half shell 22 is seen in FIG. 3. The half shells 20, 22 are secured to one another at the positions 24 by means of screws or the like.

The endoscope 10 comprises an ocular cup 26 at the proximal end, with which the image of the observation area transmitted through the endoscope shaft 12 can be observed with the eye. In addition, an ocular focusing ring 28 is provided with which the observed image can be focused.

The shaft 12 is formed by an outer shaft 30 (see FIGS. 1 and 3) as well as an inner shaft 32 arranged in the outer shaft 30. The inner shaft 32 receives the system of optical imaging elements of the endoscope, which are not shown in the figure and which are arranged in a tubular shaft (not shown) disposed in the inner shaft 32.

The shaft 12, i.e. the outer shaft 30 and the inner shaft 32, are rotatable together relative to the handle 14 about their center axis, which is indicated by the arrow 34. The inner shaft 30 and the outer shaft 32 are fixed to one another against rotation, such that they rotate commonly. The outer shaft 30 comprises a window 38 at its distal end 36 in the form of a shell, whose center point lies near the entry pupil (not shown). The window 38 forms a light entry opening of the endoscope 10. The light exit is provided for by the polished ends of optical fibers located on either side of the window 38 of the shaft 12.

An object to be observed (not shown) is seen at a view direction 40 through the window 38 with the endoscope 10. The view direction 40 is pivotal through a mechanism 41, to be discussed in more detail below. The view direction 40 can be pivoted back and forth as shown by the double arrow 42 with respect to the longitudinal direction of the shaft by means of the mechanism 41. The view direction 40 can also be pivoted back and forth in circumferential direction as indicated by the double arrow 34.

Figure 2:
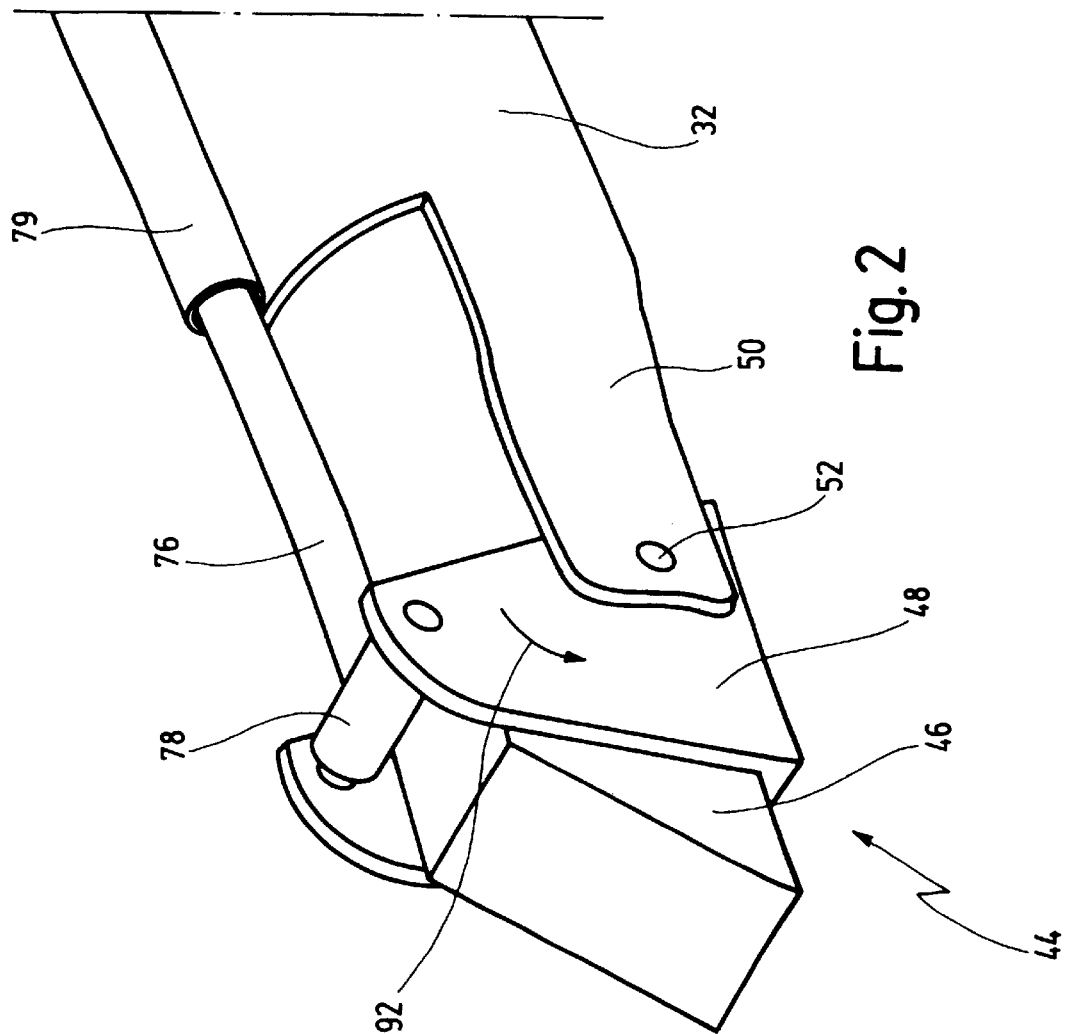
FIG. 2 shows an enlarged perspective illustration of the distal end of the endoscope in FIG. 1, where the outer shaft of the endoscope in FIG. 1 is removed.

The mechanism 41 for pivoting the view 40 according to the double arrow 42 comprises an optical element 44 arranged in the outer shaft 12 at the distal end 36, which is shown in FIG. 2 in enlarged scale. The optical element 44 is a prism 46 secured in a bracket 48, which in turn is pivotally mounted between two side sections 50 of the inner shaft 32.

The prism 46 is pivotal about the pivot axis 52 running transversely to the longitudinal direction of the shaft 12. According to this embodiment, adjustment of the optical element 44 takes place by a rotation of the prism 46 about the pivot axis 52, where the rotation of the optical element 44 produces a pivoting of the view direction with respect to the longitudinal direction, i.e. according to the double arrow 42.

A first operating element 54 is provided on the handle 14 to rotate the optical element 44 to produce a pivoting of the view direction 40 as indicated by the double arrow 42 between a forward view (view angle of about 5° with respect to the axis of the shaft 12) and a rear view (view angle of about 120°). The operating element 54 is actuated with one finger, preferably the index finger of the same hand holding the handle 14.

The mechanism 41 also includes the possibility of rotating the shaft 12 according to the double arrow 34 to thereby pivot the view in circumferential direction. A second operating element 56 is positioned on the handle 14 to pivot the view 40 in circumferential direction, where the amount of rotation in both directions can be completely 360°. The operating element 56 is positioned relative to the first operating element 54 so as to be actuatable with the thumb of the same hand holding the handle 14.

The first operating element 54 is arranged on a front or distal side 58 of the handle 14, namely approximately centrally with respect to the transverse dimension of the handle 14. The first operating element 54 is configured as a pistol-like trigger, which is pivotally mounted on the handle 14 as indicated by the double arrow 62, which will be described in detail below.

The first operating element 54 comprises a ring 64 completely closed about its periphery. The diameter of the opening in the ring 64 is dimensioned such that the index finger can pass through the ring.

The second operating element 56 is configured as an adjustment wheel 66, positioned at about the elevation of the first operating element 54, however displaced proximally therefrom on the handle 14.

The handle 14 comprises a window 70 on its side face 68 in which a portion 72 of the circumference of the adjustment wheel 66 is located, where the wheel can be actuated by the thumb.

A corresponding window is provided on the side surface of the half shell 22 on the side opposing the side face 68, so that a portion of the adjustment wheel 66 can also be actuated from this side. In this manner, the adjustment wheel 66 can be operated with the left hand or the right hand in a one-hand operation with the respective thumb. The direction of actuation of the adjustment wheel 66 is in the direction indicated by the double arrow 74, i.e. is substantially parallel to the axis of the shaft 12.

As can be taken from FIG. 1, the first operating element 54 and the second operating element 56 can be operated simultaneously, where the first operating element 54 can be operated for example with the index finger and the second operating element 56 with the thumb of the same hand holding the handle 14. The handhold is ergonomic and does not cause tiring of the hand. Thus, the view direction 40 can be simultaneously pivoted in the longitudinal direction and in the circumferential direction.

The optical element 44 is connected with the first operating element 54 for adjustment thereof as will be discussed with reference to FIGS. 2 and 3. As seen in FIG. 2, a traction element 76 is linked via a cross pin 78 to the upper end of the bracket 48. The traction element 76 is disposed in the housing 16 in a mantle 79 passing within the outer shaft 30 and on the inner shaft 32, where its other end is secured to a coupling sleeve 81 (FIG. 3). The coupling sleeve 81 is fixed to the inner shaft 32 and therefore with the shaft 12 to be fixed against rotation, so that the element 76 and the mantle tube 79 also rotate along with the shaft 12.

An approximately centrally located groove 81a is provided in the coupling sleeve 81, which accordingly is formed as two integrally connected sleeve halves 81b and 81c on either side of the groove 81a. A fork element 80 engages in the central groove 81a, which is angled but otherwise rigid. The lower portion of the fork member 80 is slidably disposed in a guide 82 according to the double arrow 83 and is connected to the first operating element 54 via a cross pin 84, where the cross pin 84 engages in a groove 86 formed as a guide curve.

Accordingly, a rotation of the first operating element 54 in the direction of the arrow 88 causes a displacement of the traction element 76 in the direction of the arrow 90. A displacement of the traction element 76 in the direction of the arrow 90 causes a pivoting of the bracket 48 about the pivot axis 52 and therefore a pivoting of the prism 46 in the direction of the arrow 92 as shown in FIG. 2. In this manner, the view direction is pivoted forwardly. By moving the first operating element 54 in the direction opposite to the arrow 88, the traction element 76 is displaced in opposite direction of the arrow 40 towards the proximal end, whereby the prism 46 is pivoted in opposite direction of the arrow 92 and the view is pivoted back in the rearward direction.

The second operating element 56 in the form of the adjustment wheel 66 is pivotally mounted in the handle 14, namely on a shaft 94 fixed to the adjustment wheel 66. The pivot axis of the wheel 66 runs transversely to the axis of the shaft 12. The transfer of the rotary movement of the adjustment wheel 66 about its axis into a rotation of the shaft 12 about its axis is accomplished through a transmission 95 in the form of a level gear assembly.

The shaft 94 carries a bevel gear 96 at its upper end, which meshes with a further bevel gear 98 fixedly secured to the inner shaft 32. A rotation of the adjustment wheel 66 about the axis of the shaft 94 thus causes a rotation of the inner shaft 32 and the outer shaft 30 fixed thereto about their common center axis. The transmission 95 formed of the bevel gears 96, 98 according to FIG. 3 has a transmission ratio smaller than 1, so that a fine adjustment of the view in circumferential direction is possible.

Again with reference to FIG. 1, markings 100 are provided on the handle 14 which indicate which direction the operating element 54 must be moved according to the double arrow 62 to pivot the view 40 in the forward direction (5°) or in the rear direction (120°).

On the whole, the handle 14 is ergonomically configured. A indentation 102 is provided on the backside of the handle 14 which supports the gap between the thumb and the index finger of the hand holding the handle. Correspondingly, a upper indentation 104 and a lower indentation 106 are formed on the front side 58 of the handle 14, where the middle finger can rest against the upper indentation 104. The little finger can rest against the indentation 106.

In addition, a connector 108 is arranged on the handle 14 at a sunk or recessed location for connecting a fiber optic cable (not shown). An opening 110 is provided on either side of the handle 14 at the position of the connector 108, which simplifies the connection of the optic cable through the connector 108. A downwardly extending passage 112 is provided at the lower end of the handle 14 for passage of the fiber optic cable, where the passageway 112 allows for a certain bending movement of the cable.

The surface of the handle 14, especially in the area 114 gripped by the hand is roughened, so that the gripping properties are improved and a slipping of the handle 14 in the hand is avoided.

A storage opening 116 is provided for secure storage of a protection cap (not shown) for the distal end 36 of the shaft 12 when the endoscope 10 is in use.

Figure 4:
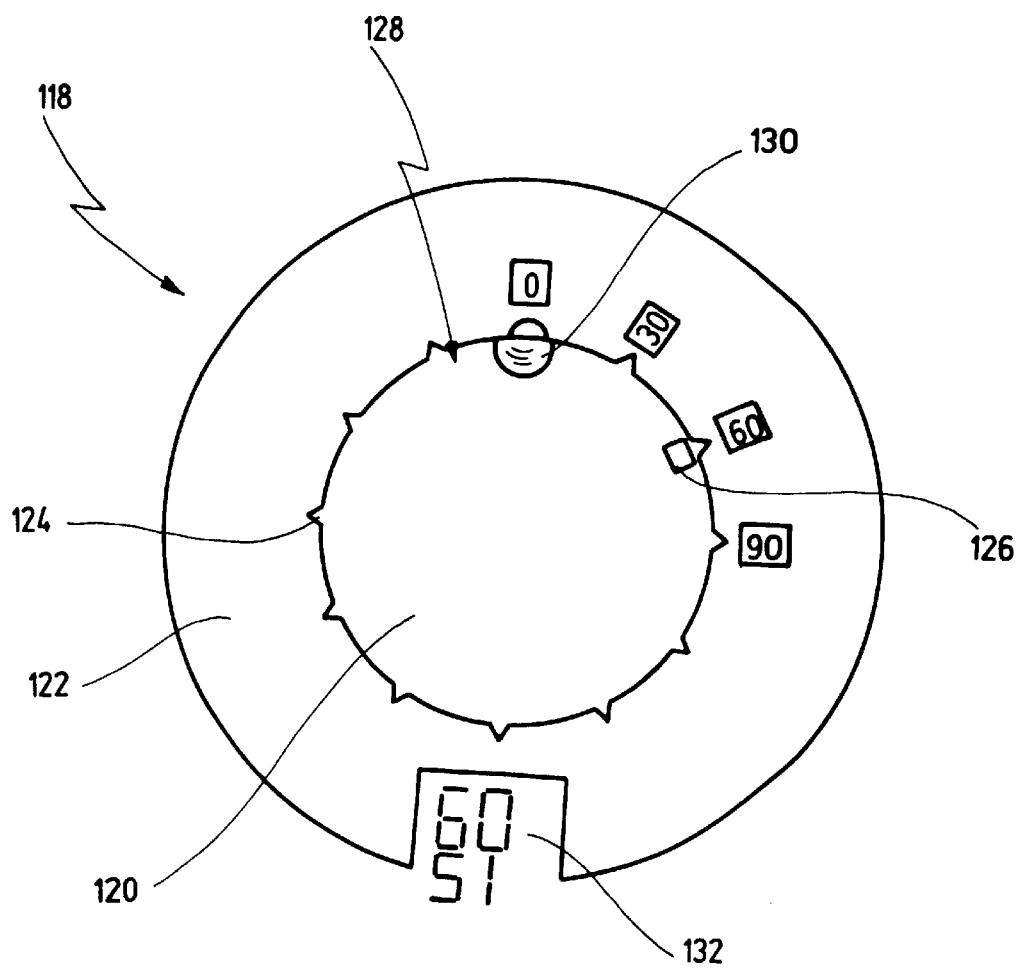
FIG. 4 shows a schematic illustration to enlarged scale of a display of the view direction shown in the view field.

Endoscope 10 further comprises display means 118 for displaying the respectively adjusted view direction, which is visible in a view field 120 when looking through the endoscope as shown in FIG. 4. The display means 118 include a disc-like element 122 having reference markings 124 on its circumference, which in the present embodiment are displaced at intervals of 30°.

The display means also include a pointer 126 rotatable relative to the disc-like element 122, whose position indicates the respective adjusted view 40 in circumferential direction. The denotations can be applied to the reference markings 124, as shown in FIG. 4, which enable a rough estimation of the adjusted view 40 in circumferential direction in combination with the pointer 124. The 0° direction here corresponds to the opposite direction of the handle 14. When the handle 14 is held vertically, the display means 118 allow the view angle 40 in circumferential direction to be read off with respect to the vertical direction. Thus the position of an object "targeted" under this view direction in the observation area can be determined and documented.

The display means 118 can be configured such that the disc-like element 122 is a shutter fixed relative to the housing 16 of the endoscope 10, while the pointer 126 is arranged to rotate with the shaft 12, or vice versa.

In addition, the display means 118 include a fluid 128, in which a gas bubble 130 is present, such as in a level. This provides further orientation for the user, because the gas bubble 130 always indicates the vertical direction, i.e. even when the handle 114 is not completely vertical, but slightly inclined.

Furthermore, the display means 118 have a digital display 132 which is also visible in the view field 120. The digital display includes a digital display of the view 40 in circumferential direction (upper number) and a display of the view 40 in longitudinal direction (lower number), which in each case indicate the angle of the adjusted view direction with respect to the vertical or with respect to the axial direction of the shaft measured in degrees.

Figure 5:
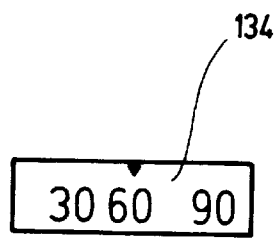
FIG. 5 shows a portion of a modified display.
Figure 6:
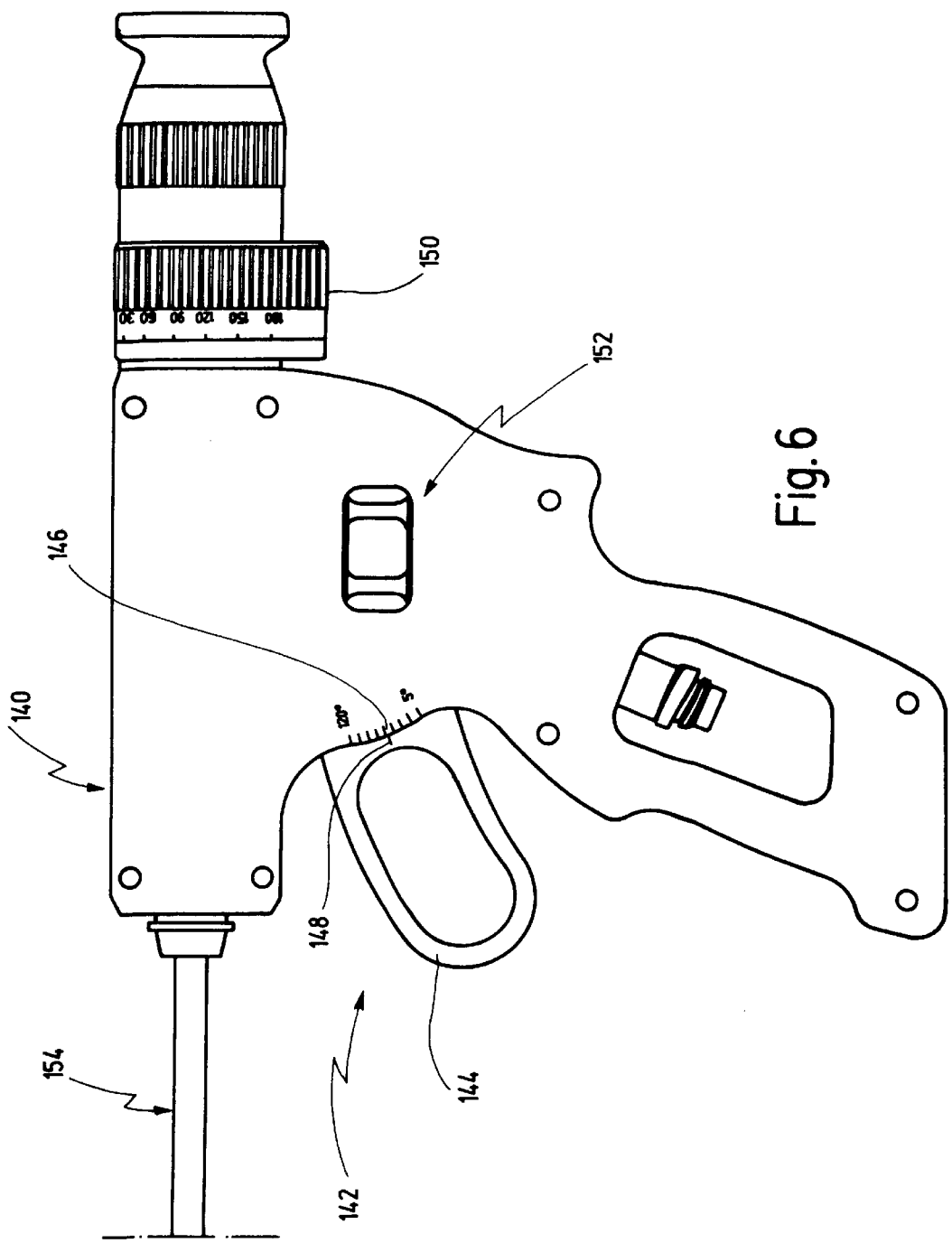
FIG. 6 shows a further embodiment of an endoscope according to the present invention.

As an alternative to the digital display 132 in FIG. 4, an analog display 134 is shown in FIG. 5 in the viewfinder field 120. A further embodiment of an endoscope 140 is shown in FIG. 6, which is modified compared to the endoscope 10 in FIGS. 1 to 3. The operating element 142 for pivoting the view in the longitudinal direction comprises a ring 144 which is also completely closed about its circumference. However, the ring 144 is dimensioned to be larger than the ring 64 in FIG. 1, so that the ring 144 is suitable for operation with two fingers, the index and the middle fingers.

In addition, markings 146 are provided indicating the directional marking for the pivoting in longitudinal direction, which act together with a marking 148 on the ring 144.

Further, the endoscope 140 includes a ring 150 for rotating the shaft 154 of the endoscope 140 as does the operating element 152, where the ring 150 allows rapid rotation over a larger angular range, while the operating element 152 in the form of an adjustment wheel allows a fine rotation of the shaft 154 and therefore a fine adjustment of the view in circumferential direction.

Figure 7:
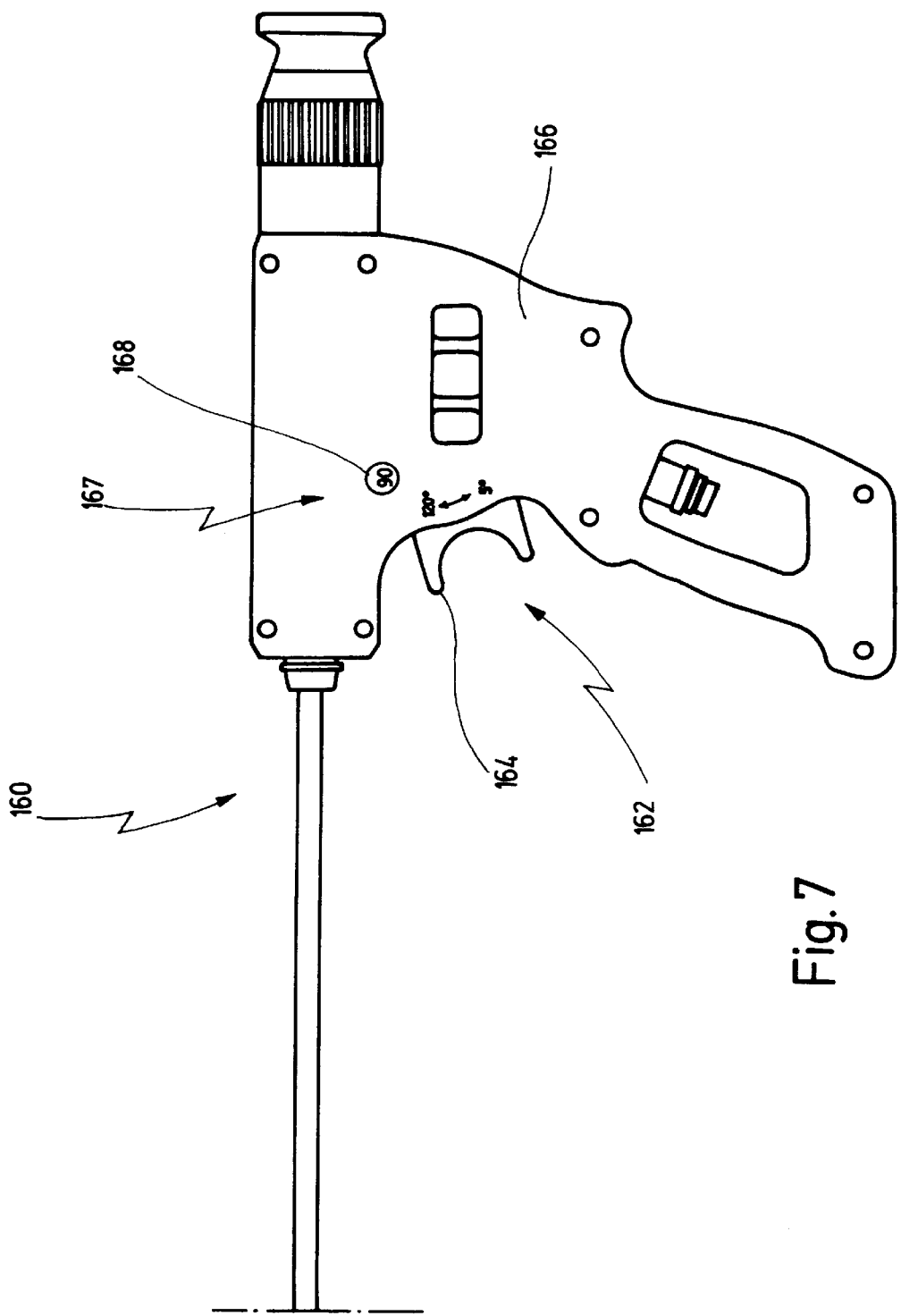
FIG. 7 shows a further embodiment of an endoscope according to the present invention.

A further embodiment of an endoscope 160 is shown in FIG. 7. The endoscope 160 differs from the endoscope 140 and the endoscope 10 in that the operating element 162 for pivoting the view in longitudinal direction is provided as a partially open ring 164 in the form of a toggle.

In addition, a display device 167 is provided on the handle 166 of the endoscope 160, which has a display window 168 through which a digital or analog display is visible for the adjusted view direction. Two such display windows 168 can be provided, namely one for the display of the view in circumferential direction and one for the display of the view in longitudinal direction.

What is claimed is:

1. An endoscope, comprising:
 a shaft having a longitudinal axis, a distal end and a proximal end;
 a handle disposed at said proximal end of said shaft and extending sidewards of said shaft, said handle being configured in pistol-like fashion;
 a mechanism for pivoting a view direction of said endoscope within an observation area; and
 at least two operating elements which are operatively engaged with said mechanism for actuating said mechanism, a first one of said at least two operating elements being for pivoting said view direction with respect to said longitudinal axis of said shaft and the second one of said at least two operating elements being for pivoting said view direction in circumferential direction, said first operating element being disposed on a front side of said handle such that it is operable with at least one finger of the hand holding said handle,
wherein said second operating element is disposed on a side face of said handle such that it is operable with the thumb of said same hand holding said handle.

2. The endoscope of claim 1, wherein said first operating element is configured as a pistol-like trigger.

3. The endoscope of claim 1, wherein at least one of said first and second operating element is configured as a button, a pair of buttons or as a toggle switch.

4. The endoscope of claim 1, wherein said first operating element comprises a ring closed or partially open at its circumference for passing or receiving one or more of said fingers.

5. The endoscope of claim 1, wherein said second operating element is formed as a slide member arranged on said at least one side face of said handle.

6. The endoscope of claim 1, wherein said second operating element is formed as an adjustment wheel rotatably mounted in said handle, where said handle comprises at least one window on at least one of its side faces, in which a portion of the circumference of said adjustment wheel is exposed.

7. The endoscope of claim 6, wherein said adjustment wheel is arranged in said handle with its pivot axis not being parallel to said longitudinal axis of said shaft.

8. The endoscope of claim 1, wherein said mechanism for pivoting said view direction comprises at least one optical element arranged to be adjustable in position at said distal end of said shaft, where the position adjustment of said optical element provides pivoting of said view direction substantially with respect to said longitudinal axis of said shaft and wherein said first operating element is operatively engaged with said optical element.

9. The endoscope of claim 1, wherein said mechanism provides rotatability of said shaft, wherein said shaft is rotatable about its longitudinal axis to pivot said view direction in circumferential direction of said shaft and wherein said second operating element is operatively engaged with said shaft for rotating said shaft.

10. The endoscope of claim 1, wherein at least one of said first and second operating elements is configured to be self-retarded.

11. The endoscope of claim 1, wherein at least one of said first and second operating elements is lockable in at least one operating position.

12. The endoscope of claim 1, wherein at least one display means is provided for displaying a respectively adjusted view direction.

13. The endoscope of claim 12, wherein said display means is arranged in the image transmission path of said endoscope so that said adjusted view direction is displayed in a viewfinder image.

14. The endoscope of claim 13, wherein said display means comprises a disc-like element having reference markings distributed about its circumference and a pointer running about said longitudinal axis of said shaft relative to said markings.

15. The endoscope of claim 1, wherein at least one display means is provided for displaying a respectively adjusted view direction and wherein said display means comprises a bubble in a fluid for indicating the vertical direction.

16. The endoscope of claim 1, wherein at least one display means is provided for displaying a respectively adjusted view direction and wherein said display means comprises a digital or analog display for said adjusted view direction.

17. The endoscope of claim 1, wherein at least one display means is provided for displaying a respectively adjusted view direction and wherein said display means comprises one or more display windows arranged on said handle to be visible from the outside with a digital or analog display for said adjusted view direction.

18. The endoscope of claim 1, wherein said handle projects from said shaft to be inclined toward said distal end of said shaft.

19. The endoscope of claim 1, wherein a connector is arranged to be sunk in said handle for connecting a fiber optic cable, where said handle comprises an opening on at least one side at the position of said connector.

20. The endoscope of claim 1, wherein a TV camera is integrated at a proximal end of said endoscope.

21. The endoscope of claim 1, wherein it is usable in technical applications, in particular in the investigation of combustion chambers.

22. The endoscope of claim 1 wherein it is usable for medical applications, in particular in endoscopic surgery.

* * * * *